(12) United States Patent
Hsu

(10) Patent No.: US 8,690,327 B2
(45) Date of Patent: Apr. 8, 2014

(54) IMAGE CAPTURE DEVICE FOR FUNDUS AND IMAGING METHOD

(75) Inventor: Cheng-Chiang Hsu, Miaoli (TW)

(73) Assignee: Altek Corporation, Hsinchu (TW)

( * ) Notice: Subject to any disclaimer, the term of this patent is extended or adjusted under 35 U.S.C. 154(b) by 91 days.

(21) Appl. No.: 13/600,524

(22) Filed: Aug. 31, 2012

(65) Prior Publication Data

US 2014/0036229 A1 Feb. 6, 2014

(30) Foreign Application Priority Data

Aug. 1, 2012 (TW) .............................. 101127723 A

(51) Int. Cl.
*A61B 3/12* (2006.01)
*A61B 3/14* (2006.01)

(52) U.S. Cl.
USPC .......................................... 351/206; 351/246

(58) Field of Classification Search
CPC ........ A61B 3/14; A61B 3/12; A61B 5/14555; A61B 5/6821; G06T 2207/30041; A61F 2009/00863; A61F 2009/00872; G03B 17/48; G06F 3/013
USPC .................................. 351/206, 205, 246, 200
See application file for complete search history.

(56) References Cited

U.S. PATENT DOCUMENTS 7,922,327 B2 * 4/2011 Su et al. ......................... 351/205

* cited by examiner

*Primary Examiner* — Hung Dang
(74) *Attorney, Agent, or Firm* — Bacon & Thomas, PLLC

(57) ABSTRACT

This invention discloses an image capture device for fundus and an imaging method thereof. The image capture device includes a lighting module, a splitter, a monochrome image sensor and an image synthesis module. The lighting module emits plurality beams of monochromatic light. The splitter is disposed on a light path of the lighting module. The splitter reflects the plurality beams of the monochromatic light to a fundus of an examinee and forms a plurality of reflecting light respectively through reflection of the fundus. The monochrome image sensor receives the plurality beams of the reflecting light and produces a monochromatic image corresponding to each beam of the monochromatic light. The image synthesis module receives each of the monochromatic images and synthesizes each monochromatic image into a color image. By such arrangements, the invention provides good quality fundus imaging and reduces costs.

12 Claims, 7 Drawing Sheets

_US 8,690,327 B2_

IMAGE CAPTURE DEVICE FOR FUNDUS AND IMAGING METHOD

CROSS-REFERENCE TO RELATED APPLICATION

This application claims the benefit of Taiwan Patent Application No. 101127723, filed on Aug. 1, 2012, in the Taiwan Intellectual Property Office, the disclosure of which is incorporated herein in its entirety by reference.

BACKGROUND OF THE INVENTION

1. Field of the Invention

The present invention relates to an image capture device and an imaging method thereof, in particular to an image capture device for fundus and an imaging method thereof, capable of capturing optical images of eyes for examining the eyes.

2. Description of Related Art

Present eye inspection devices include tonometers, optometry machines and image capture devices for fundus, wherein the image capture device for fundus is an optical inspection device for observing the fundus which is disposed at the rear of a retina of an eye. The image capture device for fundus is mainly used for examining a macular of the fundus and optic nerves to determine whether or not there is any pathological change. For example, the optical image capture device for fundus can be used for diagnosing some pathological changes of the fundus including glaucoma, optic neuritis or macular degeneration; or observing the fundus to see blood vessels directly, so that the optical image capture device for fundus can be used as a screening tool for diabetic retinopathy complications.

In general, a conventional image capture device for fundus projects a single light source onto an examinee's fundus. Now, the light source is reflected or scattered by the fundus of the examinee to form an image on an image sensor, so that ophthalmologists can observe the condition of the examinee's fundus as disclosed in Pat. No. US2011/0299036. Due to a relatively weaker reflection or scattering of the fundus, the imaging process is relatively more difficulty. However, the prior art uses a single light source for the projection, so that a good imaging result can be achieved to enhance the intensity of the light source. Now, the enhanced light source may shrink the pupil, thus reducing the inspecting area of the fundus. In addition, some prior arts apply a mydriatic agent to the examinee's eye while enhancing the intensity of the light source, but the mydriatic agent usually cause discomfort to the examinee's eye, which is actually troublesome to the examinee.

In view of the aforementioned problems, the inventor of the present invention designed and developed an image capture device for fundus and an imaging method thereof to overcome the aforementioned problems of the prior art and to improve the industrial application.

SUMMARY OF THE INVENTION

In view of the problems of the prior art, The primary objective of the present invention is to overcome the problems such as uneasy fundus imaging by providing an image capture device for fundus and an imaging method thereof.

To achieve the aforementioned problems, the present invention provides an image capture device for fundus, comprising a lighting module, a splitter, a monochrome image sensor and an image synthesis module. The lighting module emits plurality beams of monochromatic light. The splitter is disposed on a light path of the lighting module to respectively reflect the plurality beams of the monochromatic light to a fundus of an examinee, and then forming plurality beams of reflecting light through reflection of the fundus, respectively. The monochrome image sensor receives each beam of the reflecting light to generate a monochromatic image corresponding to each beam of the monochromatic light, respectively. The image synthesis module receives each monochromatic image and synthesizes each monochromatic image into a color image.

Preferably, the image capture device for fundus may further comprise a mask module closely attached onto an eye of the examinee to isolate external light from entering into an eyeball of the examinee.

Preferably, the image capture device for fundus may further comprise a positioning module for clamping or supporting a face of the examinee, so that the fundus is maintained at a position to produce the plurality beams of the reflecting light.

Preferably, the image capture device for fundus may further comprise a sensing module and a stabilizing module, the sensing module is provided for detecting a vibration of the image capture device for fundus to generate a vibration signal and the stabilizing module is provided for performing vibration compensation according to the vibration signal.

Preferably, the image capture device for fundus may further comprise an image recognition module for recognizing a predetermined image feature from each of the monochromatic images; the image synthesis module synthesizes each of the monochromatic images into the color image according to the predetermined image feature.

Preferably, the image capture device for fundus may further comprise an optical component assembly disposed on the light path between the fundus and the monochrome image sensor, so as to increase or decrease the size of an image of the plurality beams of the reflecting light formed on the monochrome image sensor.

To achieve the aforementioned objective, the present invention further provides an imaging method applicable to an image capture device for fundus, and the method comprises the steps of: providing a lighting module to emit plurality beams of monochromatic light, using a splitter disposed on a light path of the plurality beams of the monochromatic light to respectively reflect the plurality beams of the monochromatic light to a fundus of an examinee, and then forming plurality beams of reflecting light through reflection of the fundus, respectively; using a monochrome image sensor to receive each beam of the reflecting light and generate a monochromatic image corresponding to each beam of the monochromatic light, respectively; and using an image synthesis module to receive each of the monochromatic images and synthesize each of the monochromatic images into a color image.

Preferably, the imaging method may further comprise a mask module, and the imaging method further comprises the step of attaching the mask module closely to an eye of the examinee to isolate external light from entering into an eyeball of the examinee.

Preferably, the imaging method may further comprise a positioning module, and the imaging method further comprises the step of using the positioning module to clamp or support a face of the examinee to be maintained at a position to produce the plurality beams of the reflecting light.

Preferably, the imaging method may further comprise the steps of using a sensing module to sense a vibration of the image capture device for fundus to generate a vibration signal; and using a stabilizing module to perform vibration compensation according to the vibration signal.

Preferably, the imaging method may further comprise the steps of using an image recognition module to recognize a predetermined image feature from each of the monochromatic images; and using the image synthesis module to synthesize each of the monochromatic images into the color image according to the predetermined image feature.

Preferably, the imaging method may further comprise an optical component assembly disposed on the light path between the fundus and the monochrome image sensor so as to increase or decrease the size of an image of the plurality beams of the reflecting light formed on the monochrome image sensor by the optical component assembly.

In summation, the image capture device for fundus and the imaging method thereof have one or more of the following advantages:

(1) The fundus image capture device and the imaging method thereof can use the plurality beams of the monochromatic light and base on the principle of different wavelengths having different receiving levels to eyes to project light with appropriate intensity onto a fundus in order to obtain a fundus image with a broader scope effectively.

(2) The fundus image capture device and the imaging method thereof can use the monochrome image sensor in order to lower the cost effectively.

(3) The fundus image capture device and the imaging method thereof can use the monochrome image sensor to improve the resolution higher than the resolution of the color image sensor, under the condition of the same area of the image sensor, or reduce the size of the monochrome image sensor smaller than the size of the color image sensor, under the condition of the same resolution, so as to enhance the image quality or reduce the volume.

DESCRIPTION OF THE PREFERRED EMBODIMENTS

Figure 1:
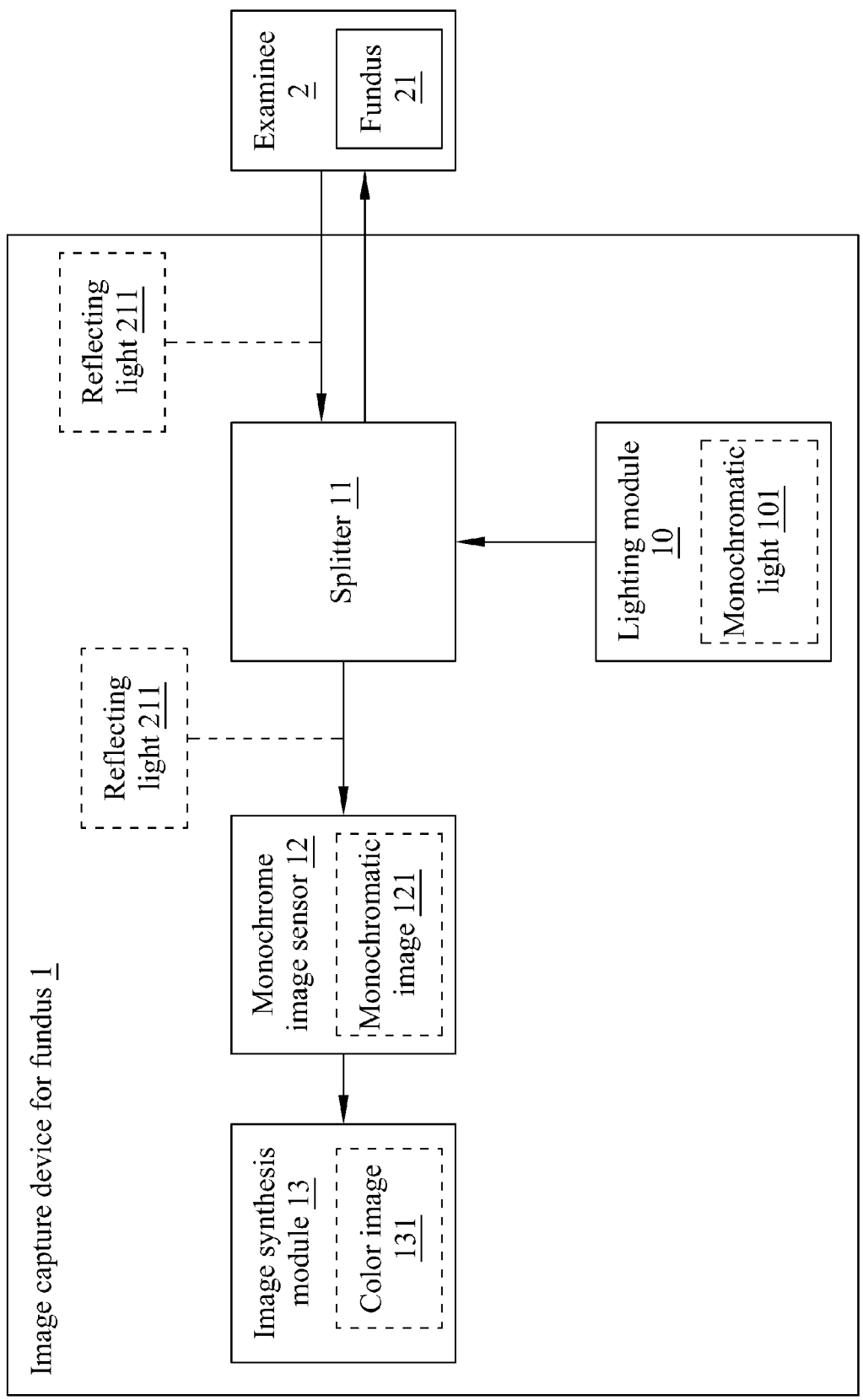
FIG. 1 is a block diagram of an image capture device for fundus in accordance with the present invention.

The technical characteristics of the present invention will become apparent with the detailed description of the preferred embodiments accompanied with the illustration of related drawings as follows. It is noteworthy to point out that the drawings are provided for the purpose of illustrating the present invention, but they are not necessarily drawn according to the actual scale, or are intended for limiting the scope of the invention, and same numerals used in the drawings represent same respective elements respectively.

With reference to FIG. 1 for a block diagram of an image capture device for fundus in accordance with the present invention, the image capture device for fundus 1 comprises a lighting module 10, a splitter 11, a monochrome image sensor 12 and an image synthesis module 13. The lighting module 10 emits plurality beams of monochromatic light 101. The splitter 11 is disposed on a light path of the lighting module 10 and provided for reflecting the plurality beams of the monochromatic light 101 to a fundus 21 of an examinee 2, and then reflecting the plurality beams of the monochromatic light 101 from the fundus 21 to form reflecting light 211, respectively. Wherein, the monochrome image sensor 12 is a complementary metal oxide semiconductor (CMOS) or a charge coupled device (CCD) for receiving each beam of the reflecting light 211 and generating a monochromatic image 121 corresponding to each beam of the monochromatic light 101. The image synthesis module 13 receives each monochromatic image 121 to form a color image 131.

It is noteworthy that the monochromatic light 101 can be red, green, blue or adjusted according to the wavelength (of a range from 400 nm to 700 nm) of human visible light. Since the light sensing level of different wavelengths varies with individuals, if light with a lower sensing level is selected as the monochromatic light 101, then a pupil of an examinee 2 will not be reduced, and a fundus image with a larger range will be available for the examination.

Figure 2:
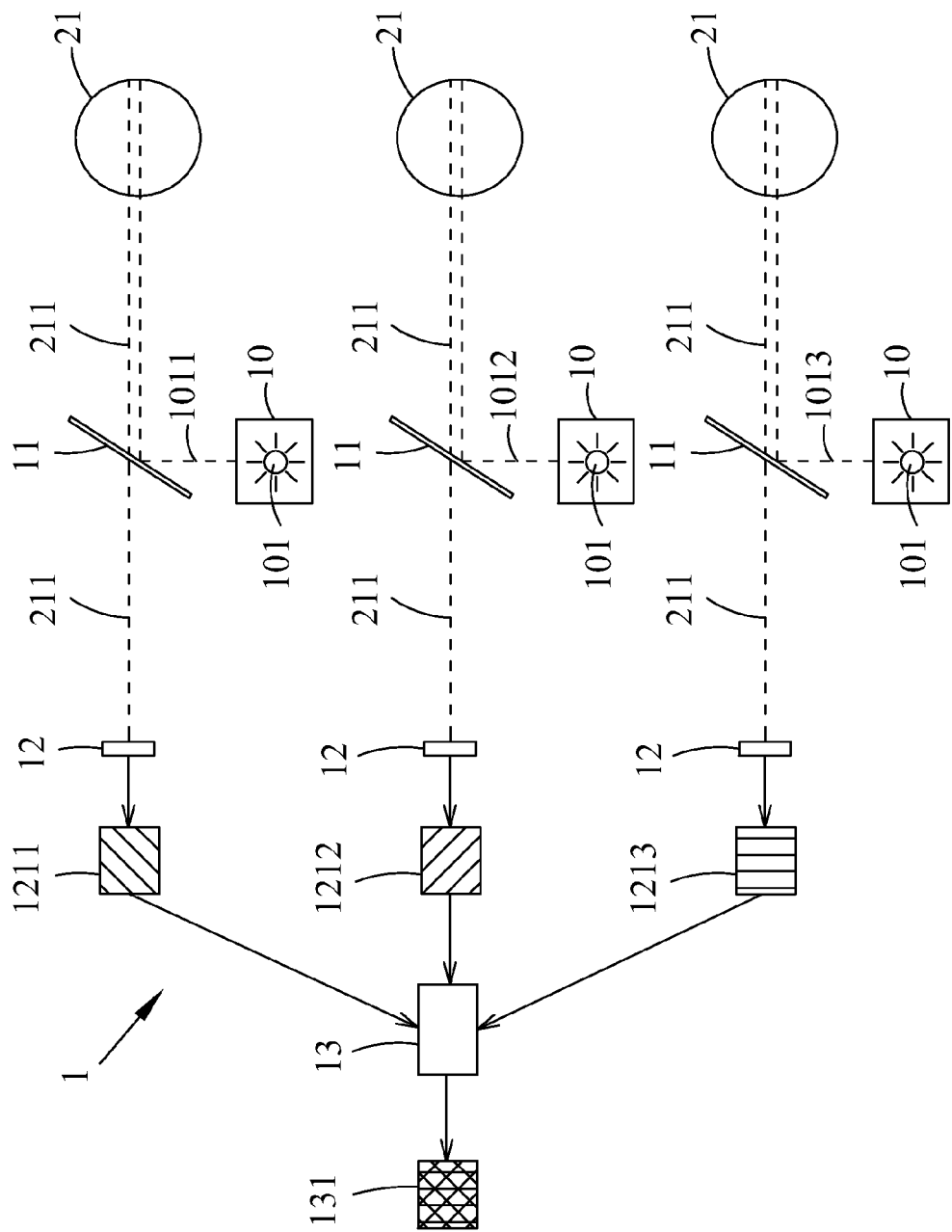
FIG. 2 is a schematic view of an image capture device for fundus in accordance with the present invention.

With reference to FIG. 2 for a schematic view of an image capture device for fundus in accordance with the present invention, when a user needs to capture an image of a fundus, the user can control or automatically turn on the lighting module 10 to emit plurality beams of monochromatic light 101 sequentially. In this preferred embodiment, three beams of the monochromatic light 101 are used as an example for illustrating the invention, but the invention is not limited to such arrangement only. When the lighting module 10 emits first monochromatic light 1011, the first monochromatic light 1011 is reflected by a splitter 11 on the light path, so that the light path is directed to the fundus 21 of the examinee 2. The fundus 21 reflects the first monochromatic light 1011 or scatters the first monochromatic light 1011 to form reflecting light 211, and the reflecting light 211 is passed through the splitter 11 and projected onto the monochrome image sensor 12. Now, the monochrome image sensor 12 converts an optical signal of the reflecting light 211 into a digital signal to generate a first monochromatic image 1211. And then, the lighting module 10 emits second monochromatic light 1012, and after a second monochromatic image 1212 is formed by the similar foregoing method, the lighting module 10 emits third monochromatic light 1013 to form a third monochromatic image 1213. After the first monochromatic image 1211, the second monochromatic light 1012, and the third monochromatic light 1013 are formed, the image synthesis module 13 synthesizes the foregoing three beams to form a color image 131. Since the image synthesis measure is well known art such as the conventional three primary color gray-scale image being synthesized to a color image, therefore it will not be described.

Figure 3:
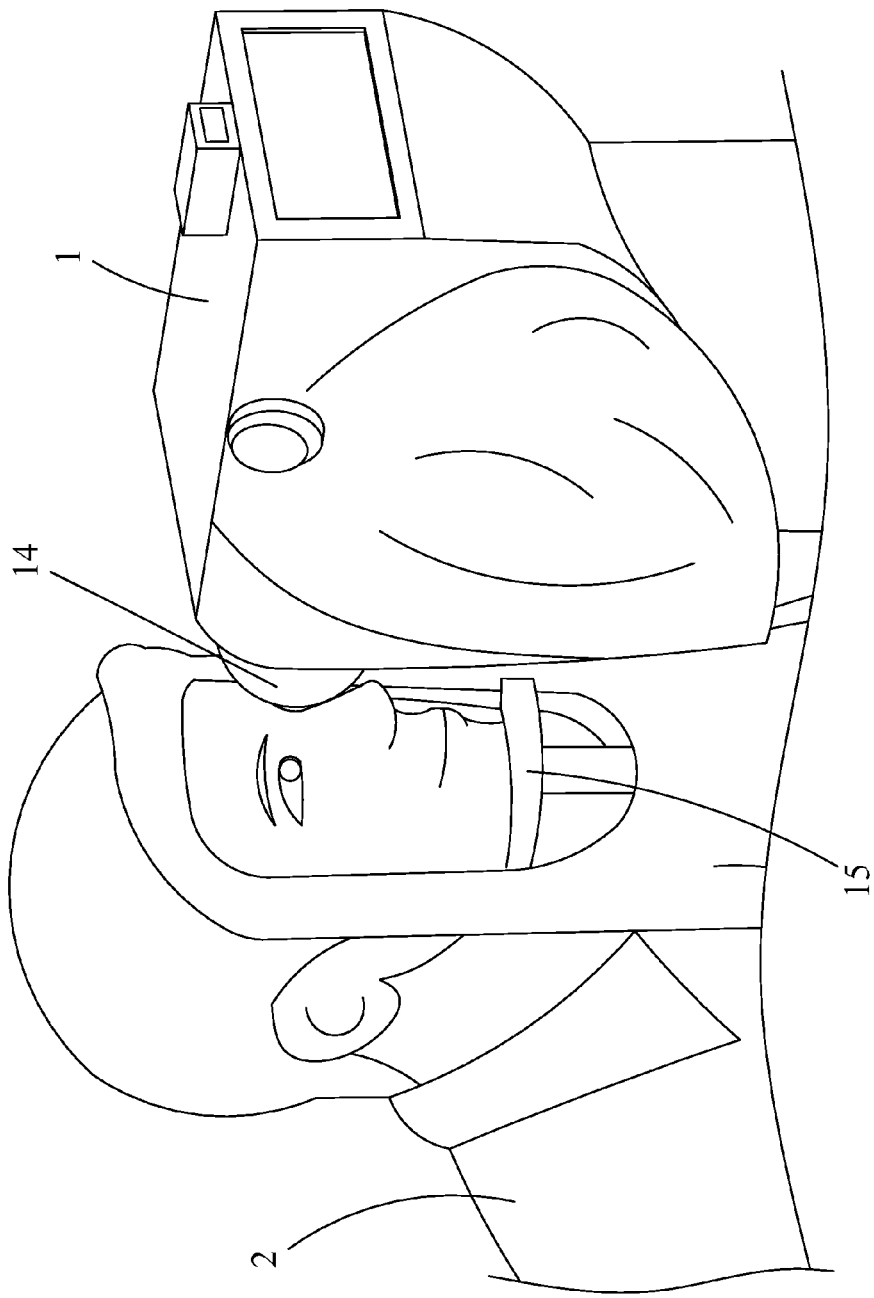
FIG. 3 is a first schematic view of an image capture device for fundus in accordance with a preferred embodiment of the present invention.
Figure 4:
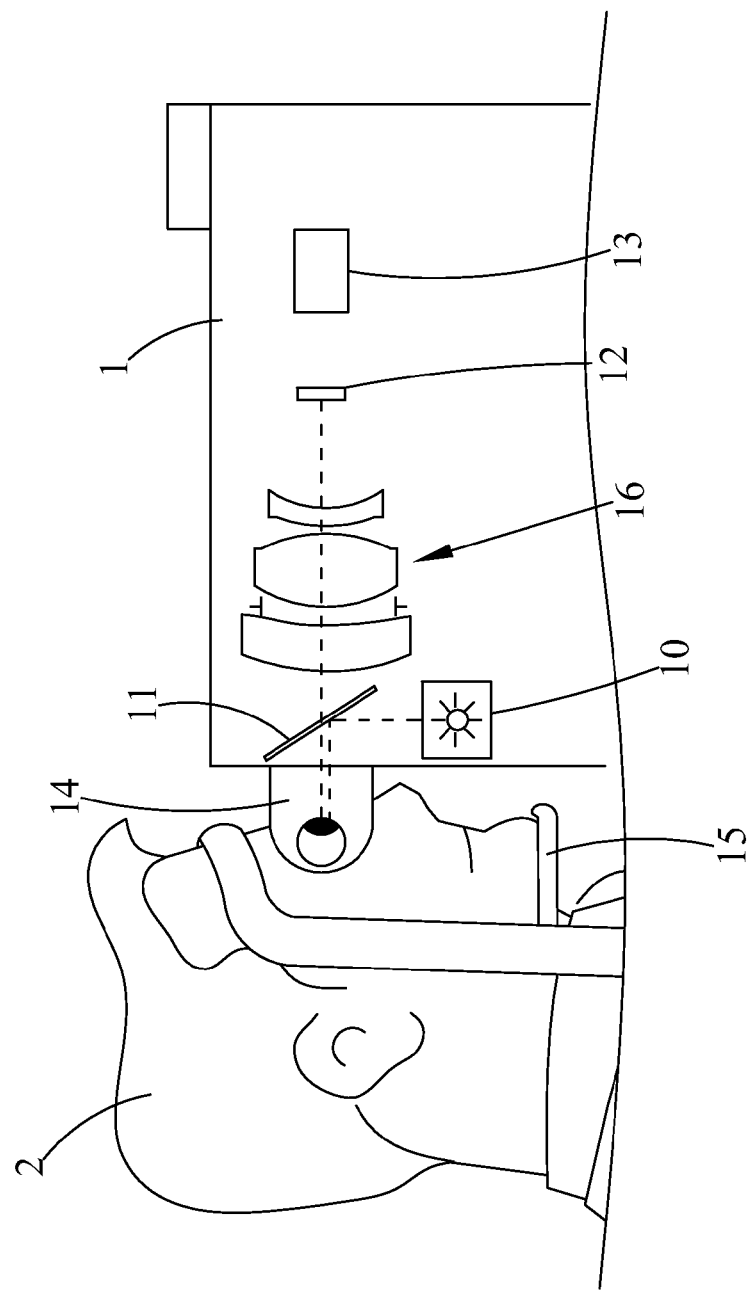
FIG. 4 is a second schematic view of an image capture device for fundus in accordance with a preferred embodiment of the present invention.

With reference to FIGS. 3 and 4 for the first and second schematic views of an image capture device for fundus in accordance with a preferred embodiment of the present invention respectively, this preferred embodiment is similar to the previous embodiment, and thus the similar parts will not be repeated. In this preferred embodiment, a general fundus camera is used as an example for illustrating the image capture device for fundus 1, wherein the image capture device for fundus 1 may further comprise a mask module 14 and a positioning module 15. The mask module 14 can be a single-eye mask or a double-eye mask made of a soft material such as foam or rubber. The positioning module 15 is provided for clamping or supporting a face of the examinee 2, so that the fundus 21 of the examinee 2 can be maintained at a position to produce each beam of the monochromatic light 101 and each beam of the reflecting light 211.

Further, when the image synthesis module 13 synthesizes the images, the position of the fundus of each monochromatic image 121 is disposed at a different position of the image; the level of difficulty for the image synthesis module 13 to synthesize the images may increase. Alternatively, vibrations may cause blurred images, and thus resulting in a poor sharpness or resolution of the color image 131 synthesized by the image synthesis module 13, and the examiner (such as a doctor) may have difficulties to examine the examinee or even may misjudge the examinee's conditions. Therefore, when the fundus of the examinee 2 is examined, the face of the examinee 2 can be placed on the positioning module 15, so that the positioning module 15 can securely support the face (particularly, the lower jaw) of the examinee 2 to maintain the fundus of the examinee 2 at the same position and minimize the vibration. On the other hand, the examinee 2 can attach the eyes closely onto the mask module 14 to isolate external light from entering into an eyeball or a fundus 21 of the examinee 2 which may affect the imaging process of each monochromatic image 121.

It is noteworthy that image capture device for fundus 1 further comprises an optical component assembly 16 having at least one lens or at least one aperture, and the optical component assembly 16 is disposed on a light path between the fundus 21 and the monochrome image sensor 12 to increase or decrease the size of an image formed by the reflecting light 211 on the monochrome image sensor 12.

Figure 5:
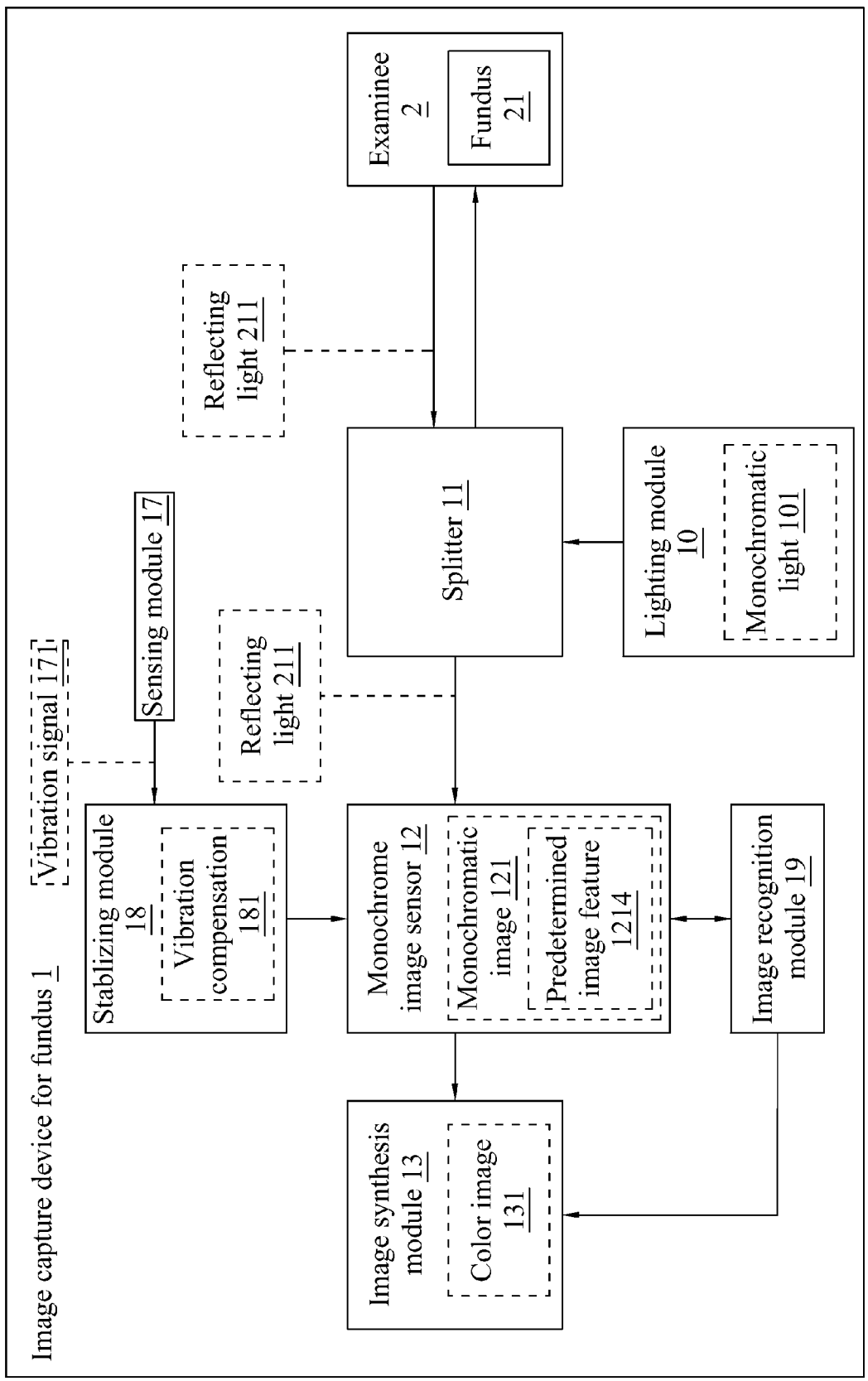
FIG. 5 is a first schematic view of an image capture device for fundus in accordance with another preferred embodiment of the present invention.
Figure 6:
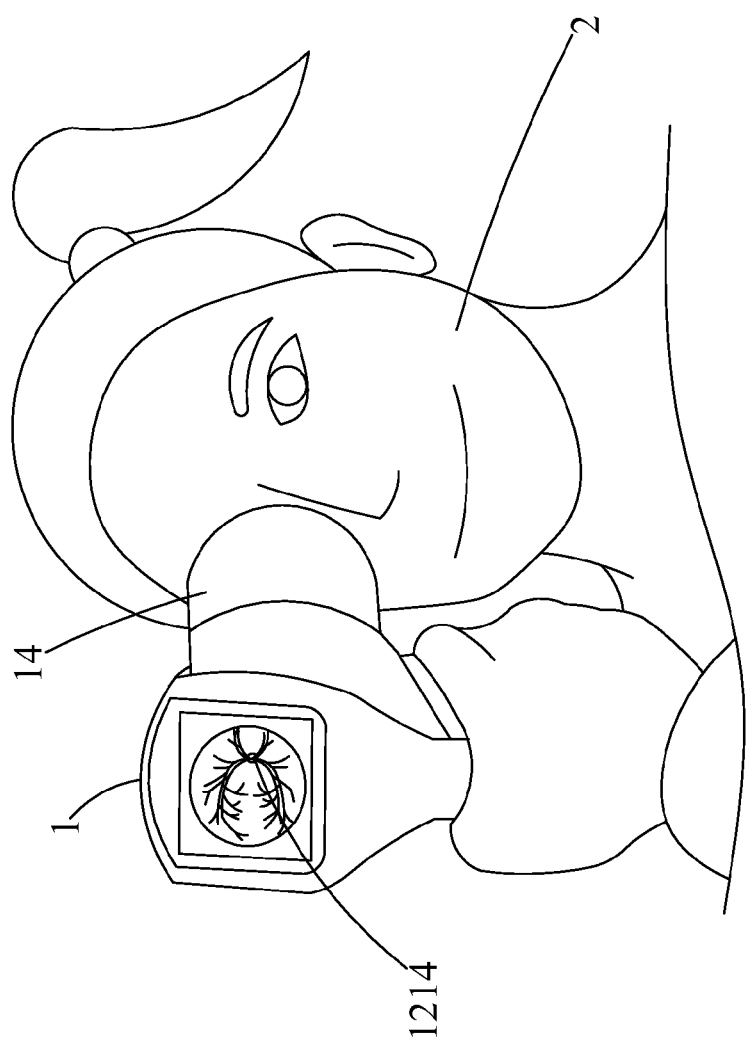
FIG. 6 is a second schematic view of an image capture device for fundus in accordance with another preferred embodiment of the present invention.

With reference to FIGS. 5 and 6 for the first and second schematic views of an image capture device for fundus in accordance with another preferred embodiment of the present invention respectively, this preferred embodiment is similar to the previous embodiment, and the similar parts will not be repeated. In this preferred embodiment, the image capture device for fundus 1 is a handheld fundus camera. The image capture device for fundus 1 may further comprise a sensing module 17 and a stabilizing module 18. The sensing module 17 comprises a position sensor and an angular velocity sensor (not shown in the figure) for sensing a vibration of the image capture device for fundus 1 to generate a vibration signal 171 and transmit the vibration signal 171 to the stabilizing module 18. The sensing module 17 obtains a displacement of the image capture device for fundus 1 from the position sensor. The sensing module 17 uses the angular velocity sensor to obtain an angular velocity change of the image capture device for fundus 1. The stabilizing module 18 performs vibration compensation 181 according to the vibration signal 171, and the vibration compensation method moves the monochrome image sensor 12 mechanically to perform the vibration compensation 181. The aforementioned measure of the stabilizing module is well known art, so that it will not be described.

When an examiner holds the image capture device for fundus 1 to examine a fundus of the examinee 2, the examiner can improve the problems of vibrations and displacements by a stabilizing module, so as to reduce the production of blurred or misaligned images.

On the other hand, the image capture device for fundus 1 further comprises an image recognition module 19. The image recognition module 19 recognizes a predetermined image feature 1214 from each monochromatic image 121 and provides the predetermined image feature 1214 to the image synthesis module 13. The image synthesis module 13 bases on the predetermined image feature 1214 as an alignment point for each monochromatic image 121 to synthesize each monochromatic image 121 into a color image 131. Wherein, the predetermined image feature 1214 can recognize, align or synthesize images with an optical disc of the fundus 21. The aforementioned image recognition measure is well-known art, and thus will not be described. After the images are recognized, a superimposition method can reduce erroneous images or superimposition failures caused by the fundus 21 that cannot be maintained on the light path.

Figure 7:
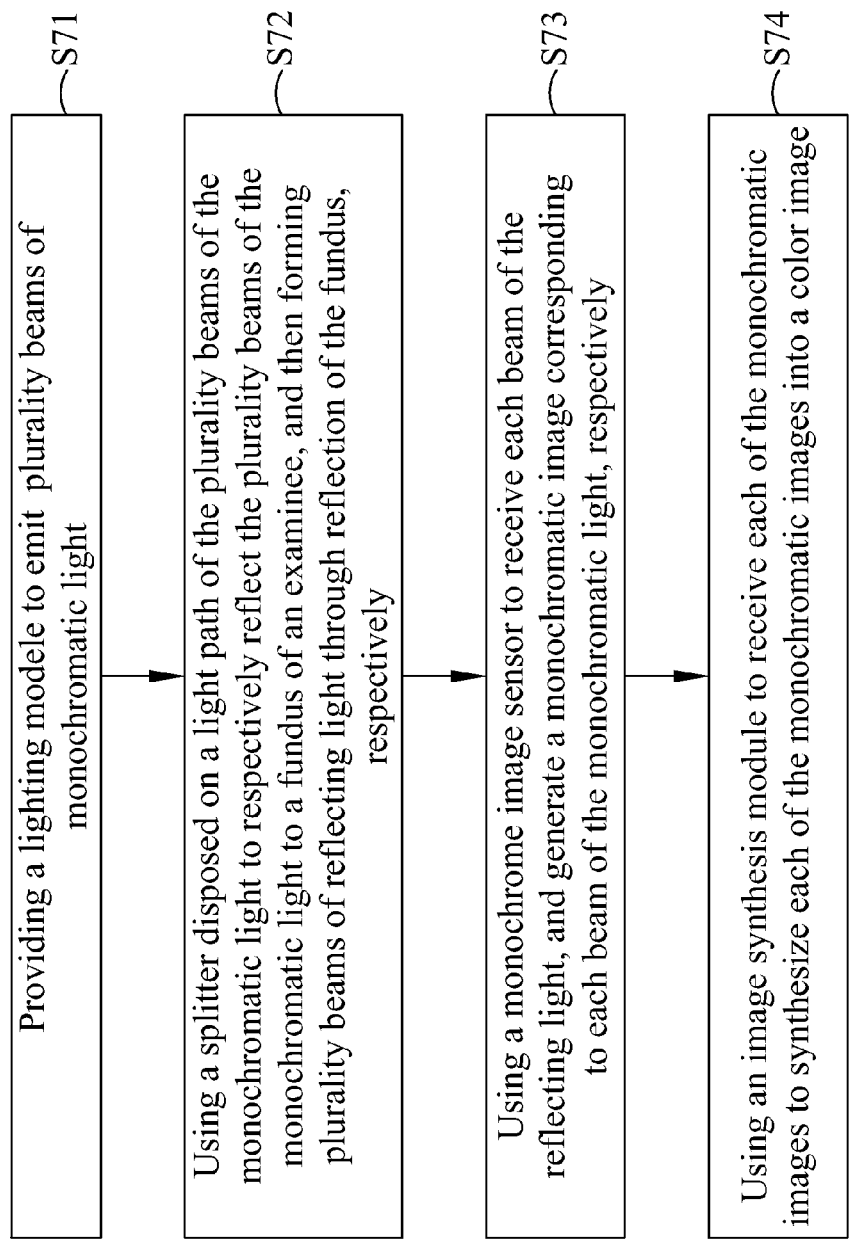
FIG. 7 is a flow chart of an imaging method of the present invention.

With reference to FIG. 7 for an imaging method of the present invention, the imaging method is applicable to an image capture device for fundus. The imaging method comprises the following steps:

(S71) Providing a lighting module to emit plurality beams of monochromatic light.

(S72) Using a splitter disposed on a light path of the plurality beams of the monochromatic light to respectively reflect the plurality beams of the monochromatic light to a fundus of an examinee, and then forming plurality beams of reflecting light through reflection of the fundus, respectively.

(S73) Using a monochrome image sensor to receive each beam of the reflecting light and generate a monochromatic image corresponding to each beam of the monochromatic light, respectively.

(S74) Using an image synthesis module to receive each of the monochromatic images, and synthesize each of the monochromatic images into a color image.

The imaging method of the image capture device for fundus in accordance with the present invention has been described in the section of the image capture device already, and thus will not be repeated.

While the invention has been described by means of specific embodiments, numerous modifications and variations could be made thereto by those skilled in the art without departing from the scope and spirit of the invention set forth in the claims.

What is claimed is:

1. An image capture device for fundus, comprising:
a lighting module, arranged for emitting plurality beams of monochromatic light;
a splitter, disposed on a light path of the plurality beams of the monochromatic light to respectively reflect the plurality beams of the monochromatic light to a fundus of an examinee, and forming plurality beams of reflecting light through reflection of the fundus;
a monochrome image sensor, arranged for receiving each beam of the reflecting light, and generating a monochromatic image corresponding to each beam of the monochromatic light, respectively; and
an image synthesis module, arranged for receiving each of the monochromatic images to synthesize each of the monochromatic images into a color image.

2. The image capture device for fundus according to claim 1, further comprising a mask module closely attached onto an eye of the examinee to isolate external light from entering into an eyeball of the examinee.

3. The image capture device for fundus according to claim 1, further comprising a positioning module arranged for clamping or supporting a face of the examinee, so that the fundus is maintained at a position to produce the plurality beams of the reflecting light.

4. The image capture device for fundus according to claim 1, further comprising a sensing module and a stabilizing module, the sensing module being arranged for detecting a vibration of the image capture device for fundus to generate a vibration signal, and the stabilizing module being arranged for performing a vibration compensation according to the vibration signal.

5. The image capture device for fundus according to claim 1, further comprising an image recognition module arranged for recognizing a predetermined image feature from each of the monochromatic images, wherein the image synthesis module synthesizes each of the monochromatic images into the color image according to the predetermined image feature.

6. The image capture device for fundus according to claim 1, further comprising an optical component assembly disposed on the light path between the fundus and the monochrome image sensor, so as to increase or decrease a size of an image of the plurality beams of the reflecting light formed on the monochrome image sensor.

7. An imaging method, applicable to an image capture device for fundus, comprising the steps of:
providing a lighting module to emit plurality beams of monochromatic light;
using a splitter disposed on a light path of the plurality beams of the monochromatic light to respectively reflect the plurality beams of the monochromatic light to a fundus of an examinee, and then forming plurality beams of reflecting light through reflection of the fundus, respectively;
receiving each beam of the reflecting light by using a monochrome image sensor, and generating a monochromatic image corresponding to each beam of the monochromatic light, respectively; and
receiving each of the monochromatic images and synthesizing each of the monochromatic images into a color image by an image synthesis module.

8. The imaging method of claim 7, further comprising a mask module, and the imaging method further comprising the step of: attaching the mask module closely onto an eye of the examinee to isolate external light from entering into an eyeball of the examinee.

9. The imaging method of claim 7, further comprising a positioning module, and the imaging method further comprising the step of: clamping or supporting a face of the examinee to be maintained at a position to produce the plurality beams of the reflecting light by the positioning module.

10. The imaging method of claim 7, further comprising the steps of: sensing a vibration of the image capture device for fundus to generate a vibration signal by a sensing module; and
using a stabilizing module to perform a vibration compensation according to the vibration signal.

11. The imaging method of claim 7, further comprising the steps of:
recognizing a predetermined image feature from each of the monochromatic images by an image recognition module; and
synthesizing each of the monochromatic images into the color image according to the predetermined image feature by the image synthesis module.

12. The imaging method of claim 7, further comprising an optical component assembly disposed on the light path between the fundus and the monochrome image sensor, so as to increase or decrease a size of an image of the plurality beams of the reflecting light formed on the monochrome image sensor by the optical component assembly.

* * * * *